United States Patent
Peltier

(10) Patent No.: US 10,240,183 B2
(45) Date of Patent: Mar. 26, 2019

(54) METHOD AND APPARATUS FOR PREPARING A CELLULAR CONTAINER COMPRISING MEANS FOR PRE-ANALYSIS OF A SAMPLE THAT HAS BEEN TAKEN

(71) Applicant: NOVACYT, Velizy Villacoublay (FR)

(72) Inventor: Eric Peltier, Clamart (FR)

(73) Assignee: NOVACYT, Velizy Villacoublay (FR)

( * ) Notice: Subject to any disclaimer, the term of this patent is extended or adjusted under 35 U.S.C. 154(b) by 8 days.

(21) Appl. No.: 14/911,017

(22) PCT Filed: Aug. 8, 2014

(86) PCT No.: PCT/EP2014/067116
§ 371 (c)(1),
(2) Date: Feb. 8, 2016

(87) PCT Pub. No.: WO2015/018933
PCT Pub. Date: Feb. 12, 2015

(65) Prior Publication Data
US 2016/0201108 A1    Jul. 14, 2016

(30) Foreign Application Priority Data
Aug. 9, 2013  (FR) ...................... 13 57924

(51) Int. Cl.
| | | |
|---|---|---|
| *C12Q 1/24* | (2006.01) | |
| *G01N 1/14* | (2006.01) | |
| *G01N 9/24* | (2006.01) | |
| *G01N 21/59* | (2006.01) | |
| *G01N 9/00* | (2006.01) | |
| *G01N 35/10* | (2006.01) | |

(52) U.S. Cl.
CPC ................. *C12Q 1/24* (2013.01); *G01N 1/14* (2013.01); *G01N 9/00* (2013.01); *G01N 9/24* (2013.01); *G01N 21/59* (2013.01); *G01N 35/10* (2013.01); *G01N 35/1009* (2013.01); *G01N 2035/1048* (2013.01); *G01N 2035/1062* (2013.01)

(58) Field of Classification Search
CPC . C12Q 1/24; G01N 9/24; G01N 21/59; G01N 35/1009; G01N 9/00; G01N 35/10; G01N 2035/1062; G01N 1/14; G01N 2035/1048
See application file for complete search history.

(56) References Cited

U.S. PATENT DOCUMENTS

| | | | |
|---|---|---|---|
| 2006/0105462 A1* | 5/2006 | Sellek-Prince | G01N 1/2813 436/55 |
| 2007/0041875 A1 | 2/2007 | Bach et al. | |
| 2007/0084990 A1 | 4/2007 | Coates | |
| 2010/0163111 A1 | 7/2010 | Tajima | |
| 2010/0221772 A1 | 9/2010 | Peltier | |
| 2010/0288941 A1 | 11/2010 | Ayliffe et al. | |
| 2012/0142043 A1 | 6/2012 | Koyata et al. | |
| 2013/0224851 A1* | 8/2013 | Ljungmann | G01N 1/31 435/288.7 |

FOREIGN PATENT DOCUMENTS

| | | |
|---|---|---|
| EP | 0 556 971 A2 | 8/1993 |
| EP | 2 535 712 A1 | 12/2012 |
| WO | WO 2011/117523 A1 | 9/2011 |

\* cited by examiner

*Primary Examiner* — Renee Claytor
*Assistant Examiner* — Susan E. Fernandez
(74) *Attorney, Agent, or Firm* — Knobbe, Martens, Olson & Bear, LLP

(57) ABSTRACT

A method for preparing a cell suspension for analysis includes at least: taking a sample of the cell suspension using a pipetting-dispensing device, which includes at least one pipe, and depositing the sample present in the pipetting-dispensing device in an analysis container. Between the taking of the sample and the depositing, the method includes at least one pre-analysis of the sample, which is carried out by a pre-analysis device placed on the pipe of the pipetting-dispensing device.

4 Claims, 2 Drawing Sheets

METHOD AND APPARATUS FOR PREPARING A CELLULAR CONTAINER COMPRISING MEANS FOR PRE-ANALYSIS OF A SAMPLE THAT HAS BEEN TAKEN

FIELD OF THE INVENTION

The present invention relates to a method for preparing a cell suspension for analysis, of the type comprising at least the following successive steps:

(a) taking a sample of the cell suspension using a pipetting-dispensing device, said pipetting-dispensing device comprising at least one pipe;

(b) depositing the sample present in the pipetting-dispensing device in an analysis container.

The invention also relates to an apparatus for preparing a cell suspension for analysis able to carry out such a method.

BACKGROUND OF THE INVENTION

The preparation method and apparatus according to the invention are for example designed to prepare a cell analysis slide as part of medical screening or diagnostics from cytological samples, such as Pap smears or other procedures.

The cells that are taken are placed in a sample vial, where the cells are placed in solution. Part of the cell solution is next taken and placed in an analysis container for diagnostic analysis of the sample. Document WO-2011/117523 for example describes such a preparation apparatus.

However, the analysis container obtained does not always make it possible to obtain a relevant and definite diagnosis, for example because the sample taken does not contain enough cells or because the cells of interest for diagnostic purposes are not in that sample. The obtained analysis container is then unusable.

In some applications, such as smear tests to screen for cervical cancer, cells are spread on analysis slides, and this spread must contain a satisfactory number of cells under the Bethesda classification, which is a classification for standardizing diagnostic smear test results. Each spread must thus contain more than 5000 cells.

In document FR-2,922,019, a method is disclosed for measuring the cell density done in the decanting chamber situated above the analysis slide. The density measured, for example by light diffraction, is subsequently compared to a threshold density corresponding to the minimum cell density of the spread on the analysis slide necessary to make a relevant diagnosis. Thus, if the density is below the threshold density, the method comprises an additional step for adjusting the cell density of the spread by adding, in the decanting chamber, a greater quantity of cell suspension taken from the vial than the standard quantity in order to produce a second representative smear slide.

However, this type of measurement in the decanting chamber has the drawback of being done after a first cell deposition. If there are not enough cells on the analysis slide, it is necessary to take the cell suspension again to produce a second smear. This therefore involves carrying out an additional complete step for depositing cells on the slide.

SUMMARY OF THE INVENTION

One aim of the invention is to offset these drawbacks by proposing a preparation method and automaton making it possible to adjust the cell density and reduce the preparation time for analysis containers to a single standardized step, while guaranteeing a quality of these containers making it possible to obtain a reliable diagnosis.

To that end, the invention relates to the analysis or pre-analytic verification method for the preparation of a cell suspension of the aforementioned type, wherein between the sample-taking step and the depositing step, the method comprises at least one step for pre-analysis of the sample that has been taken, said step being carried out by means of a pre-analysis device placed on the pipe of the pipetting-dispensing device.

This method makes it possible to guarantee the quality of the containers by providing pre-analytical information about the cell suspension from the sample that has been taken by the practitioner, i.e., in the vial. By analyzing the sample that has been taken, for example to determine whether it contains enough cells, before making the analysis container, it is guaranteed that the sample used to make this container is relevant. This pre-analysis is done in the pipetting-dispensing device, which avoids having to perform a second analysis spread if the pre-analysis is not satisfactory. The production of a second slide by the pipetting-dispensing device is avoided, and the production of analysis containers that can later be analyzed reliably is guaranteed in a pre-analytic, and not post-analytic, step.

According to another aspect of the invention, the method includes one or more of the following features, considered alone or according to any technically possible combination(s):

the pre-analysis step is a step for measuring the cell density of the sample that has been taken;

the step for measuring the cell density further comprises a step for comparing the measured cell density to a reference density;

if the measured cell density is lower, respectively higher, than the reference density, step (a) further comprises at least one of the following steps:

(f) taking a volume of the cell suspension larger than a standard volume, respectively smaller than the standard volume, using the pipetting-dispensing device so as to obtain smears with a homogenous density;

(g) establishing information relative to the volume that has been taken in order to ensure traceability of the sample handling steps, said steps being carried out until a threshold of the number of cells that have been taken guaranteeing the relevance of the analysis is reached;

the cell density is measured by emitting light in the pipe through the sample and measuring the attenuation or diffraction of light having crossed through the sample; and the pipetting-dispensing device comprises at least one needle suitable for taking a sample of the suspension, the pipe extending between the needle and suction-discharge means, the sample-taking step (a) being arranged so that at least part of the sample that has been taken passes through the pipe across from the pre-analysis device.

The invention also relates to a cell analysis preparation apparatus of the type comprising:

at least one vial containing a cell suspension to be analyzed;

at least one analysis container, at least one pipetting-dispensing device comprising at least one pipe, the pipetting-dispensing device being able to take a sample of the cell suspension to be analyzed and pour it into the analysis container;

wherein the pipetting-dispensing device comprises a pre-analysis device arranged on the pipe of the pipetting-dispensing device, said device being able to perform a pre-analysis step of the sample in said pipe.

According to other features of the apparatus according to the invention:

the pre-analysis device comprises means for emitting a signal through the pipe of the pipetting-dispensing device, means for receiving the modified signal having crossed through said pipe, and means for analyzing said signal.

BRIEF DESCRIPTION OF THE DRAWINGS

The invention will be better understood upon reading the following detailed description, provided solely as an example, done in reference to the appended drawings, in which.

DETAILED DESCRIPTION OF CERTAIN EMBODIMENTS OF THE INVENTION

In the description, the terms "upstream" and "downstream" are defined relative to the flow direction of a detergent liquid in the needle, the liquid being discharged in the needle by discharge means positioned upstream from the needle. Consequently, the dispensing from the needle is done in an upstream-downstream direction, while the suction is done in a downstream-upstream direction.

Figure 1:
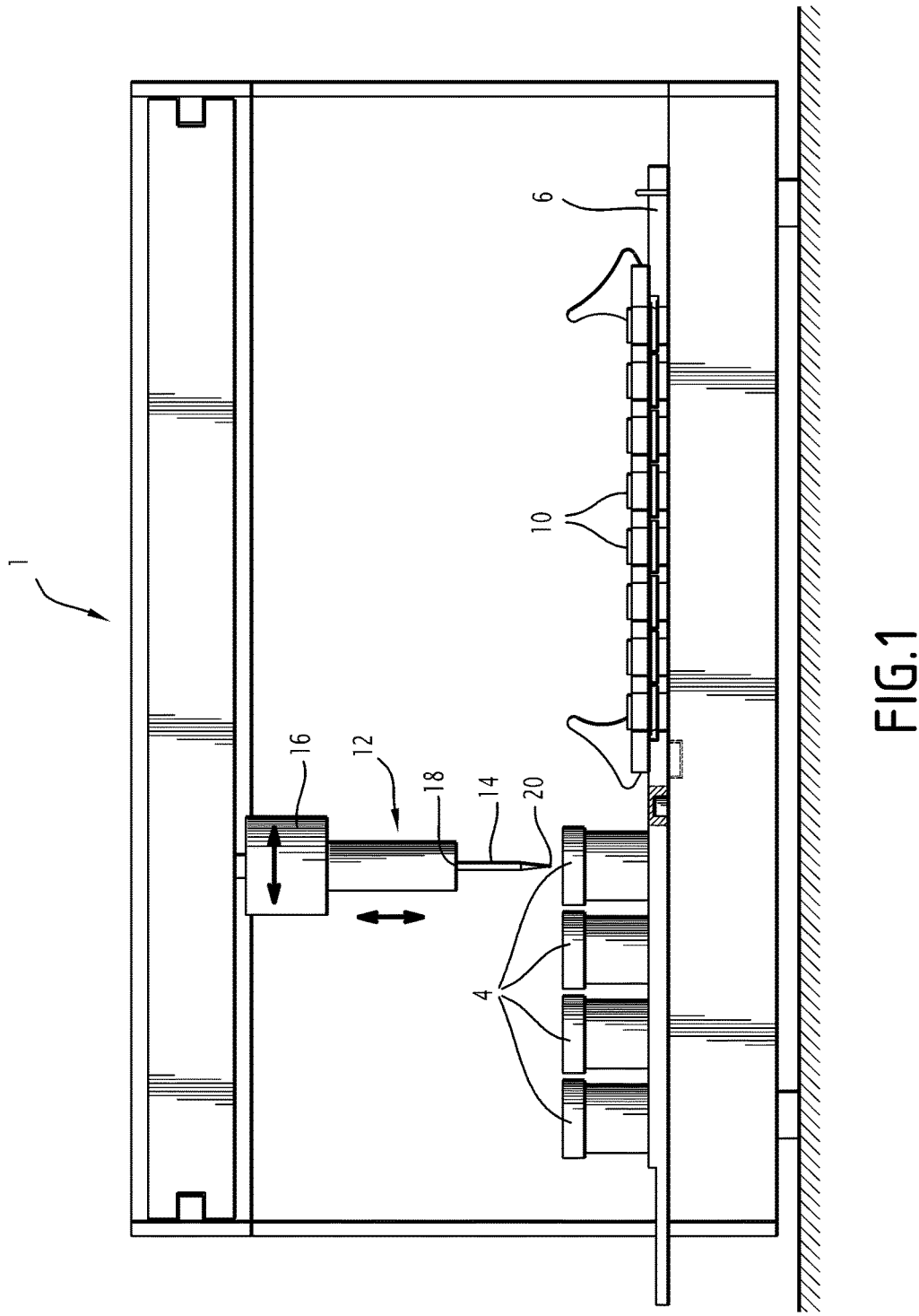
FIG. 1 is a schematic sectional view of a sample-taking and analysis automaton comprising an analysis preparation apparatus according to the invention.

FIG. 1 shows an automaton 1 for preparing and analyzing at least one vial 4 containing a cell suspension 5 to be analyzed (FIG. 2), for example a fixed cytological suspension. The cell suspensions 5 are obtained by suspending cell samples for example obtained during a cervical smear test procedure or by other types of sample-taking. The manner in which the sample that has been taken is placed in suspension and in which the cells are preserved is known and will not be described in detail here.

The automaton 1 essentially comprises a receiving plate 6 for the vials 4 and decanting chambers 10 arranged above analysis slides on which thin-layer cell smears must be done from cell suspensions 5, using a pipetting-dispensing device 12 able to take samples of the cell suspensions 5 and deposit the samples in the decanting chambers 10, optionally going through intermediate treatment steps.

Because the automaton 1 and its operation have been described in document WO-2011/117523, the automaton will not be described here in more detail. One skilled in the art can refer to this document to see all of the other features, details and alternative embodiments. It is understood that the automaton can be adapted for producing types of analysis containers other than analysis slides. For example, the analysis containers 22 of this preparation and analysis system 20 can include, depending on the analysis chosen by the practitioner, smear slides, withdrawal or aliquoting tubes, and analysis or decanting wells.

The pipetting-dispensing device 12, or sampling device, extends above the receiving plate 6 and is able to take, move and pour or discharge various liquid products, in particular samples of cell suspensions 5. To that end, the pipetting-dispensing device 12 comprises a plurality of tubular and hollow needles 14, or pipettes, movable between the different stations of the automaton 1 by an arm 16 and movable vertically to make it possible to lower and raise the needles 14.

Each needle 14 extends between an upstream end 18 and a downstream end 20 in fluid communication with one another.

The operations for taking samples of a cell suspension 5 are done by suction through the downstream end 20 of the needle 14, and the pouring or evacuation operations are done by discharging, or dispensing, through that downstream end 20. To that end, the upstream end 18 of the needle is in fluid communication with suction and discharge means 22 positioned upstream from the needle 14 and arranged to allow suctioning of products and discharging of those products through the downstream end 20 of the needle. To that end, the suction and discharge means 22 are connected to the upstream end 18 of the needle 14 by a pipe 24, for example a flexible pipe allowing the movement of the needle 14 relative to the suction and discharge means 22, as shown in FIG. 2.

The suction and discharge means 22 are for example formed by a traditional suction-discharge pump for this type of application. Alternatively, the suction and discharge means 22 could be formed by a piston and/or valve system, or other system. The suction and discharge means 22 make it possible to carry out steps involving the pipetting-dispensing device 12 in the operation of the automaton 1. A level sensor 25 is provided at the pipe 24 between the upstream end 18 of the needle 14 and the suction and discharge means 22 in order to determine the presence or absence of products in the pipe 24.

The pipetting-dispensing device 12 also comprises pre-analysis means 26 for the sample taken by the needle 14. These pre-analysis means 26 are provided on the pipe 24, i.e., upstream from the needle 14 and downstream from the suction and discharge means 22, for example near the upstream end 18 of the needle 14.

Figure 2:
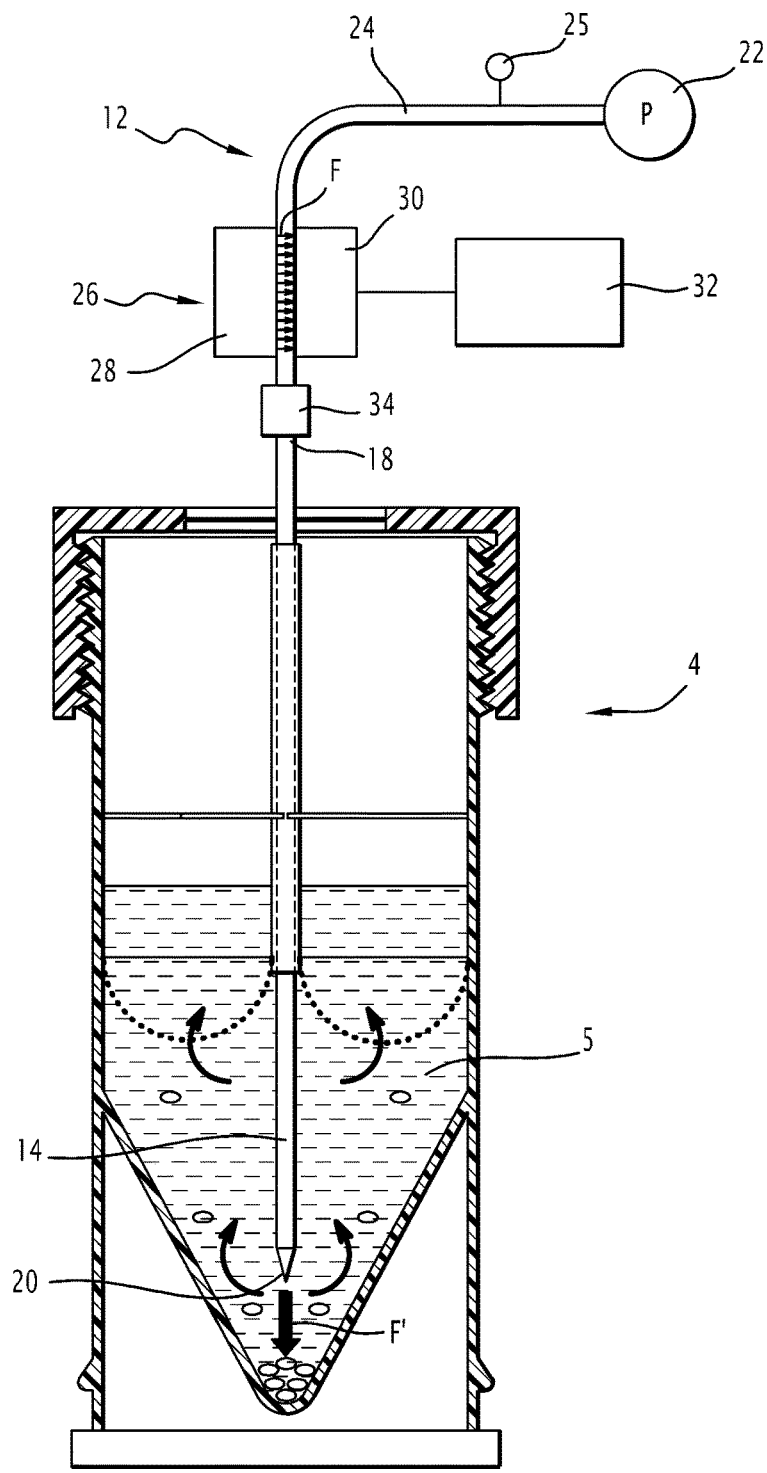
FIG. 2 is a sectional view of a vial during a sample-taking step of the method for preparing a cell suspension for analysis according to the invention.

These pre-analysis means are suitable for allowing pre-analysis of a sample taken immediately from the cell suspension 5, as shown in FIG. 2, or immediately after a treatment step of the sample, such as a cell marking step. Cell marking refers to introducing a particular marker in the sample or in the cell suspension or a step for dyeing the sample or the cell suspension. This pre-analysis consists of measuring the cell density of the sample.

The pre-analysis means 26 comprises at least means 28 for transmitting a signal F, means 30 for receiving the signal F after it has crossed through the pipe 24, and means 32 for analyzing the signal received by the receiving means 30. The transmission means 28 and the receiving means 30 are arranged on either side of the pipe 24, such that the signal transmitted by the transmission means 28 is received on the other side of the pipe 24 by the receiving means 30 after the signal F has crossed through the pipe 24 and its contents.

As an example, the transmission 28 and receiving 30 means could be provided in a connector 34 arranged to fasten the needle 14 and the pipe 24 together or be provided in a sleeve designed to surround the pipe 24.

In order to measure a cell density, the transmission means 28 are for example a light source, such as one or more light-emitting diodes, laser (tunable laser, polychromatic light source, etc.), arranged to emit a light signal through the pipe, and the receiving means 30 are for example a sensor of the light signal, such as a photodiode (APD, CCD strip, CCD CMOS camera or spectrometer), having crossed through the pipe.

The analysis means 32 are then for example means for measuring the absorption of the light signal received by the receiving means 30 or means for measuring the diffraction of light by the cells present in the pre-analyzed sample. Such methods for measuring cell density by measuring the absorption of the light or diffraction are known and will not be described in more detail here.

The pre-analysis step is carried out as follows: the sample that has been taken is suctioned in the pipe at least until it comes across from the pre-analysis means 26, which can be determined using the level sensor 24. The pre-analysis means are then activated and the received signal, modified relative to the signal emitted after its passage through the sample, is sent to the analysis means 32, which determines the cell density of the sample.

In the case of measurement of the cell density in the sample, the analysis means 32 compares the measured density to a so-called reference density. The reference density is the cell density necessary to obtain a relevant cell density and number of cells in the analysis container 22 to be able to make a diagnosis.

If, in a first case, the measured cell density is above the reference density, the needle 14 takes, from the vial, a volume of the cell suspension smaller than the standard volume, normally taken when the cell density corresponds to the reference density. Then, the needle 14 moves, via the robotic arm 16, above an analysis container 10 or other parts of the automaton if steps for treating the sample are envisaged. The sample contained in the pipe 24 is poured into the analysis container 10 or is treated, for example in a receiving well or tube for an additional or other technique or analysis.

If, in a second case, the measured cell density is below the reference density, the needle 14 takes a volume of the cell suspension from the vial larger than the standard volume, so as to increase the number of cells taken and arrive at a threshold guaranteeing the relevance of the analysis.

The apparatus and method described above for preparing a cell suspension for analysis make it possible to obtain, directly in the analysis containers, optimized cell samples for conducting a relevant analysis leading to an interpretation of the screening or diagnostics. The sample is analyzed immediately before being taken or before treatment, which thus avoids performing a second smear.

Determining the cell density allows a pre-analytic characterization of the cell suspension and the establishment of information on the volume of the suspension taken in order to ensure traceability of the treatment steps of the sample so as to inform the person or resources in charge of the analysis about the representativeness of the initial withdrawal.

The pre-analysis means 26 can also be used to verify the proper operation of the automaton 1. Indeed, if the automaton is arranged to perform a treatment of the cell suspension, for example dyeing or marking, it is possible to determine whether this treatment has been done correctly by passing a sample from the treated suspension through the pre-analysis means 26, and thus verifying that the characteristics of the sample obtained at the end of the treatment indeed correspond to the expected characteristics following the treatment operation. The pre-analysis means therefore allow qualitative monitoring of the automaton.

Furthermore, the apparatus can be adapted to a plurality of needles, so as to be able to perform several pre-analyses at the same time, and therefore in particular to automate the preparation and analysis of a plurality of suspensions.

The invention claimed is:

1. A method for preparing a cell suspension for analysis, comprising at least the following successive steps:
   (a) taking a first portion of a sample of the cell suspension using a pipettor, said pipettor comprising at least one pipe; and
   (b) pre-analyzing the entire first portion of the sample that has been taken by a pre-analysis analyzer placed on the pipe of the pipettor, said pre-analyzing comprising measuring the cell density of the first portion of the sample that has been taken and comparing the measured cell density to a reference density,
   wherein,
      (i) if the measured cell density is lower than the reference density, the pre-analyzing further comprises taking a second portion of the sample of the cell suspension using the pipettor so that a combined volume of the first portion and the second portion in the pipettor has a volume of the cell suspension that is larger than a standard volume, or
      (ii) if the measured cell density is higher than the reference density, the pipettor is used to take a volume of the first portion of the sample of the cell suspension, wherein the volume is smaller than the standard volume, so as to obtain deposit smears with a homogenous density, and
   (c) depositing the sample present in the pipettor in an analysis container,
   wherein steps (a)-(c) are repeated to provide a number of deposited smears of homogenous density for analysis.

2. The method according to claim 1, further comprising: establishing the volume that has been taken.

3. The method according to claim 1, wherein the cell density is measured by emitting light in the pipe through the sample and measuring the attenuation or diffraction of light having crossed through the sample.

4. The method according to claim 1, wherein the pipettor comprises at least one needle suitable for taking a sample of the suspension, the pipe extending between at least one of the at least one needle and a suction-discharger, wherein in step (a), at least part of the sample that has been taken passes through the pipe across from the pre-analysis analyzer.

* * * * *